United States Patent [19]

Pinzon

[11] Patent Number: 6,159,479
[45] Date of Patent: *Dec. 12, 2000

[54] HYDROUS SALICYLIC ACID SOLUTIONS

[75] Inventor: Carlos O. Pinzon, Clark, N.J.

[73] Assignee: L'oreal, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/931,309

[22] Filed: Sep. 16, 1997

[51] Int. Cl.⁷ .............................. A61K 9/08; A61K 7/48; A61P 17/12

[52] U.S. Cl. .......................... 424/401; 514/848; 514/859; 514/975

[58] Field of Search .............................. 424/484, 62, 401; 514/975, 848, 844, 859

[56] References Cited

U.S. PATENT DOCUMENTS

| | | |
|---|---|---|
| 4,767,750 | 8/1988 | Jacquet et al. . |
| 5,409,640 | 4/1995 | Giret et al. . |
| 5,439,682 | 8/1995 | Wivell et al. . |
| 5,443,817 | 8/1995 | Zimmerman et al. . |
| 5,683,975 | 11/1997 | Skodell et al. . |

*Primary Examiner*—Edward J. Webman
*Attorney, Agent, or Firm*—Oblon, Spivak, McClelland, Maier & Neustadt, P.C.

[57] ABSTRACT

A composition containing a salicylic acid derivative, a solubilizer, a coupler, and water.

16 Claims, No Drawings

HYDROUS SALICYLIC ACID SOLUTIONS

BACKGROUND OF THE INVENTION

1. Field of the Invention

The invention relates to hydrous (aqueous) salicylic acid derivative solutions useful as cosmetic and/or dermatological formulations. Preferably, the hydrous salicylic acid solutions of the invention are clear, not cloudy, and are stable over the long term.

2. Discussion of the Background

The use of salicylic acid derivatives as keratolytic agents for treating acne and as anti-ageing agents is known. FR 2,581,542 and EP 378,936 describe such derivatives. However, salicylic acid derivatives are, in general, present in crystalline form and are not sufficiently soluble in water or oils traditionally used in the cosmetic and dermatological field. Accordingly, salicylic acid derivatives tend to remain crystalline within various compositions, which significantly reduces the bioavailability of the compound. In addition, the presence of crystalline salicylic acid derivatives provides formulations which are unstable due, for example, to settling, and which are unpleasant with regard to texture and appearance from the consumer's viewpoint.

SUMMARY OF THE INVENTION

Accordingly, it is one object of the present invention to provide stable hydrous salicylic acid derivative compositions useful as cosmetic and/or dermatologic formulations.

It is another object of the present invention to provide stable hydrous salicylic acid derivative solutions.

It is another object of the present invention to provide cosmetic and dermatological compositions which contain salicylic acid derivatives formulated so as to be acceptable to the consumer and, preferably, stable and clear.

It is another object of the present invention to provide a method for treating or preventing acne, signs of ageing (wrinkling, appearance of fine lines, pigmentation, etc.), warts, freckles, etc. (hereinafter "skin features") by applying to the skin feature and, optionally, the surrounding skin, the invention hydrous salicylic acid derivatives solutions, compositions, mixtures and formulations.

These and other objects are provided hydrous salicylic acid derivative solutions comprising, among other optional components, one or more salicylic acid derivatives, one or more couplers, and one or more solubilizers.

The invention salicylic acid derivative includes compounds of formula I and topically acceptable salts thereof:

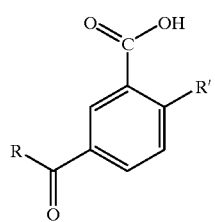

(I)

in which:

R is a linear, branched or cyclic saturated aliphatic group or an aliphatic unsaturated group containing one or a number of double bonds, which may or may not be conjugated, these groups containing from 2 to 22 carbon atoms and being able to be substituted by at least one substituent selected from (a) halogen atoms, (b) the trifluoromethyl group, (c) hydroxyl groups in the free form or esterified by an acid having from 1 to 6 carbon atoms or (d) a carboxyl functional group which is free or esterified by a lower alcohol having from 1 to 6 carbon atoms;

R' is a hydroxyl group or an ester functional group of formula:

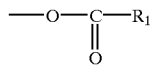

where $R_1$ is a linear or branched saturated or unsaturated aliphatic group having from 1 to 18 carbon atoms.

In addition, salicylic acid derivatives described in U.S. Pat. No. 5,558,871, FR 2,581,542, U.S. Pat. No. 4,767,750, EP 378,936, U.S. Pat. No. 5,267,407, U.S. Pat. No. 5,667,789, U.S. Pat. No. 5,580,549, and EP-A-570,230, all incorporated herein by reference, may be used in the invention.

Further, particularly preferred salicylic acid derivatives useful herein include 5-n-octanoyl salicylic acid (capryloyl salicylic acid), 5-n-decanoyl salicylic acid, 5-n-dodecanoyl salicylic acid, 5-n-heptyloxy salicylic acid and 4-n-heptyloxy salicylic acid. A highly preferred salicylic acid derivative is capryloyl salicylic acid (Trade name: Mexoryl SAB); see page 139 of the International Cosmetic Ingredient Dictionary, 6th Edition, Volume 1, published by the Cosmetic Toiletries, and Fragrance Association, 1995, incorporated herein by reference.

With regard to formula I above, the R group contains from 2 to 22 carbon atoms, inclusive of each and every carbon atom in between this range, including subranges. Useful carbon numbers include 4, 6, 8, 10, 12, 14, 16, and 18. For the R' group of formula I above, each and every carbon number between 1 and 18 is specifically included, and as are all subranges. Useful carbon numbers include 2, 4, 6, 8, 10, 12, 14, and 16. All odd carbon numbers between 2 and 22 carbon atoms for R, and all odd numbered carbon numbers between 1 and 18 for R', are also specifically included.

Useful salts of the invention salicylic acid derivative may be obtained by salification with a base. Useful bases include inorganic basis such as alkali and alkaline metal hydroxides (sodium hydroxide, potassium hydroxide, and the like) or ammonia hydroxides. Organic bases may also be used for salification. Also useful are amphoteric bases. See U.S. patent application Ser. No. 08/627,965, incorporated herein by reference, for useful salicylic acid derivatives and useful salts thereof. Quatemium salts such as dimethylhydroxypropyl ammonium salts are also particularly useful.

The present invention solutions, compositions, formulations, mixtures and the like may, include one or a mixture of the salicylic acid derivatives described above. Generally, it is preferred that the salicylic acid derivatives of the invention be present in invention solutions, mixtures, formulations, compositions, gels, and the like in amounts of from 0.1–65% by weight based upon total weight of composition, preferably 1–30% by weight, more preferably 2 wt % or more including 3, 4, 5, 6, 7, 8, 9, 10, 12, 14, 16, 18, 20, 22, 24, 26, 28 weight percent, and the like.

The present invention solubilizer has a slightly higher lipophilic affinity than the invention couplers and functions to solubilize the invention salicylic acid derivative in fluid form and enhance its bioavailability to the skin. While octyldodecanol (Eutanol G) and similar $C_{10}$–$C_{30}$ linear and branched alcohols may be used, preference is given to compounds of the following formula:

$$R(OCH(CH_3)CH_2)_nOH$$

where R is a $C_1$–$C_{22}$ linear, branched or cyclic saturated aliphatic group or unsaturated aliphatic group containing 1 or a number of double bonds. n varies from 2–22. Preferred solubilizers conformed to the above formula where R is a $C_8$, $C_{10}$, $C_{12}$, $C_{14}$, $C_{16}$ or $C_{18}$ group and n is 3, 4, 5, 6, 7, 8, 9, 10, 11 or 12. R is preferably linear or branched alkyl, most preferably linear alkyl. These compounds may be generally described as polypropylene glycol alkyl ethers (PPG-alkyl-ethers) and may also be referred to as PPG-n-C_ethers where the n and C variables correspond to the n and R variables in the above formula. Specific preferred examples of invention solubilizers include PPG-3-myristyl ether and PPG-10-cetyl ether. See the International Cosmetic Ingredient Dictionary, 6th Edition, Volume 1, CTFA, 1995, incorporated herein by reference, for further specific information regarding these and related solubilizers. The cetyl group corresponds to $R=C_{16}$ in the above formula, the myristyl group corresponds to $C_{14}$.

In the present invention a mixture of one or more solubilizers may be used, and the solubilizer(s) typically are present in amounts of from 0.1–50 wt. %, more preferably 1–20 wt. %, most preferably 2–10% by weight, all based on total weight of composition, including 3, 4, 5, 6, 7, 8, and 9 wt %.

As mentioned above, solubilizers such as octyldodecanol (see page 637–638 of the International Cosmetic Ingredient Dictionary, 6th Edition, Volume 1, CTFA, 1995, incorporated herein by reference) may be used although the PPG-alkyl-ethers mentioned above are preferred. Useful solubilizers thus include compounds of the formula $RCH(R')CH_2OH$ where R is a linear or branched, saturated or unsaturated aliphatic group having 1 to 18, preferably 4–12, more preferably 6–10 carbon atoms and R' is a linear, branched, saturated or unsaturated aliphatic group having 2–12, preferably 4–10, most preferably 6–8 carbon atoms. These solubilizers may be used alone, in mixtures of two or more, or in mixtures where the above PPG-alkyl-ethers are present. The total amount of solubilizer present is as described above regardless of the presence of solubilizers like octyldodecanol.

The invention couplers generally are water soluble emollients which exhibit a high affinity for water while still retaining much lipophilic character. These characteristics allow for the coupling between water and the solubilizer and salicylic acid derivative of the present invention. Useful couplers herein include ethoxylated fatty acid esters, in particular ethoxylated triglyceride esters, and allkylpolyglucoside ethers. The latter materials are preferred as they provide excellent results and are more mild than ethoxylated coupler materials.

Useful couplers herein include, particularly, PEG-8 caprylic/capric glycerides and PEG-6 caprylic/capric glycerides. In addition, other PEG alkyl glycerides may be used, having, generally, 2–12 mols of ethylene oxide and a carbon chain of from 4–16, preferably 6–14, more preferably 8, 10 or 12. See the definitions of PEG-6 caprylic/capric glycerides and PEG-8 caprylic/capric glycerides at pages 682 and 683 of the International Cosmetic Ingredient Dictionary, 6th Edition, Volume 1, 1995, CTFA, incorporated herein by reference. Such compounds are polyethylene glycol derivatives of mono-, di- and triglycerides of $C_4$–$C_{16}$ acids with an average of 2–12 mols of ethylene oxide.

Another type of coupler which may be used herein is PEG-n-glyceryl-esters which correspond to the general formula:

$$RCOOCH_2CH(OH)CH_2(OCH_2CH_2)_nOH$$

where R is a linear or branched saturated or unsaturated aliphatic group having from 2–24, preferably 4–20, more preferably 6–18 carbon atoms and where n represents the average value of polyethylene glycol units therein. Specific examples of these materials are PEG-7 glyceryl cocoate PEG-8 glycerylcocoate, etc. Preferred n values in the above formula vary from 3–40, including 5, 10, 15, 20, 25 and 30. See pages 696–701 of the International Cosmetic Ingredient Dictionary, 6th Edition, 1995, Volume 1, CTFA, incorporated herein by reference. These PEG-n-glyceryl esters may be used in combination with $C_6$–$C_{24}$ fatty acids and/or a polyethylene glycol ether of glycerine with an average ethoxylation value of from 7–20. See Glycereth-7, -12 and -20 at page 401 of the above-identified International Cosmetic Ingredient Dictionary, incorporated herein by reference.

Particularly preferred couplers herein are alkylpolyglucoside ethers such as caprylyl/capryl glucoside and decylglucoside. See pages 139 and 286 of the above-identified International Cosmetic Ingredient Dictionary, incorporated herein by reference. Other examples of useful alkyl glucosides herein are analogous to decylglucoside and include those products obtained from the condensation of $C_5$–$C_{24}$ alcohols with a glucose polymer. Carbon numbers of the alcohol of 6 and above are preferred. Similarly, compounds analogous to caprylyl/capryl glucoside having the formula:

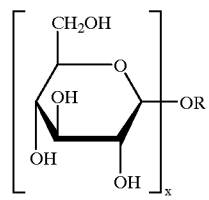

where R represents a linear or branched saturated or unsaturated aliphatic group having from 4–22 carbon atoms preferably 6–18 carbon atoms, including 8, 10, 12, 14 and 16 carbon atoms, may be used. X may vary, and is not limited. Polymeric structures are preferred.

The invention coupler component may comprise more than one class of couplers mentioned above and may comprise mixtures of different couplers of the same type. Preferably, the invention coupler is present in an amount of from 5–75% by weight, based upon total amount of composition, preferably 15–50 wt. % including 20, 25, 30, 35, 40 and 45 wt % as well as 55, 60, 65 and 70 wt % and is preferably adjusted so as to provide a clear, stable product.

The present invention solutions, mixtures, formulations, compositions, gels, and the like preferably contain water in amounts of from 1–94.8 wt. %, preferably 10–90%, including 20, 30, 40, 50, 60, 70, 75, 80 and 85 wt. %. More preferably, water is present in at least 40 wt. % and above, most preferably 50–90 wt. %. The water used is preferably pure or obtained from springs, etc. known throughout the world to have a reputation for providing good water. Deionized water is used in a preferred embodiment.

The pH of the invention solutions, compositions, formulations, mixtures, gels, and the like is preferably adjusted to a final level of from 0.5–11, more preferably 1–10, most preferably 2–8, including 2.5, 3, 3.5, 4, 4.5, 5, 5.5, 6, 6.5, 7, 7.5, and 8. All ranges and subranges are included. In a highly preferred embodiment the pH is acidic. pH's of between 2 and 3 or between 3 and 4 are most preferred. Any conventional pH adjusting agent may be used to prepare the final pH of the invention, such as citric acid, potassium hydroxide, any known buffer, and the like.

As is typical in cosmetic/dermatological compositions, other ingredients may be present in any of the invention solutions, formulations, compositions, mixtures, gels, and the like. These further components include preservatives, colorants, moisturizers, active agents such as drugs, vitamins, and the like, perfume, UV absorbers, UV screening agents, proteins or protein hydrolysates, amino acids, polyols, urea, alpha-hydroxy acids, salicylic acid itself, sugar, sugar derivatives, gelling agents such as xanthan gum, carboxylvinyl polymers, cellulose derivatives, pectins, polyacrylamides, and the like. Useful cometic and pharmaceutical agents which may be added to the invention solutions, mixtures, compositions, formulations, and the like include retinoic acid, retinol, ascorbic acid, vitamin E, retinyl palmitate, retinyl acetate, hydrocortisone, and the like.

The invention compositions, solutions, etc. may further contain ingredients which diminish the irritating effects of the salicylic acid derivatives, such as substance P antagonists, CGRP antagonists, and the like. See, for example, EP 680749, EP 716850, EP 723774, EP 737471 and EP 770392, all incorporated herein by reference.

Invention solutions, formulations, mixtures, compositions, gels, and the like may be made by those of ordinary skill in the art using techniques well known in the art. A preferred method of preparing invention compositions is mixing of the invention solubilizer and salicylic acid derivative, and subsequently adding this mixture to an aqueous phase containing the invention coupler. Depending upon the identity of the coupler, its amount, and the optional presence of other ingredients, invention compositions may be prepared having viscosities similar to water and greater, including gel-like and gel compositions. In the most preferred embodiments of the present invention the invention mixtures, solutions, formulations, compositions, gels, and the like are clear upon visible inspection and stable, preferable remaining unchanged at room temperature for a period of at least 12 weeks with no precipitation, separation of phases, appreciable or loss of clarity. In a highly preferred embodiment, the invention provides solutions, formulations, mixtures, compositions, gels, etc. which undergo little or no change when subjected to a temperature of 45° C. for twelve weeks, to six freeze/thaw cycles, or to cold conditions such as 5° C.

The present invention solutions, formulations, mixtures, compositions, gels, etc. may also have viscosities less than water, and may take the form of any conventional cosmetic and dermatological formulations known in the art regardless of viscosity. For example, the present invention may take the form of an emulsion using art-known emulsifiers and techniques for producing emulsions. The emulsions may be oil-in-water or water-in-oil emulsions. Pastes and creams are also forms which may be taken by the invention. Such forms and their production are well known to those of ordinary skill in the art. See the International Cosmetic Ingredient Dictionary, Vols. 1 and 2, 1995, CTFA, incorporated herein by reference, for known emulsifiers, oils, surfactants, etc.

The invention salicylic acid derivatives are keratolytic, and promote cell renewal among other effects and have been found to provide results and effects typically associated with alphahydroxy acids. However, it has been found that the invention salicylic acid derivatives are more potent, and provide a more effective profile than commonly used alphahydroxy acids (for example, a 2% caproyl salicylic acid formulation according to the invention may be compared with a 10% lactic acid formulation). Accordingly, the uses to which the present invention may be put include all of those known for alphahydroxy acids including all of those uses and methods listed in U.S. Pat. Nos. 5,547,998, 5,422,370, 5,389,677, 5,385,938, 5,091,171, 5,554,597, 5,554,651, 5,554,652, 5,554,654, 5,556,882, 5,561,153, 5,561,155, 5,561,156, 5,561,157, 5,561,158, 5,561,159, 5,565,487, 5,470,880, 5,643,952, 5,643,953, 5,643,961, 5,643,962, 5,643,963, 5,654,336 and 5,654,340, all incorporated herein by reference. The methods of use of the invention compounds thus include the treatment and prevention of signs of ageing, the treatment of wrinkles, etc. In addition, the treatment of skin pigmentation, warts, etc., is also included. These methods are effected by applying the invention solution, formulation, mixture, composition, gel, etc. to the skin where effects are desired. Treatment may be pin-point application to a specific location or feature, or may be topical generally including the location of the feature.

EXAMPLES

The following examples illustrate the invention without being limiting.

Compositions were prepared by mixing together the listed ingredients. First the solubilizer and active ingredient were mixed together and this mixture was added to water in the presence of coupler.

TABLE #1

| Phases | Wt. % | Wt. % |
| --- | --- | --- |
| Diluent: | | |
| Water | 72.00 | 67.00 |
| Coupler: | | |
| L.A.S. | 20.00 | 25.00 |
| Solubilizer: | | |
| Promyristyl PM-3 | 5.00 | |
| Procetyl-10 | | 5.00 |
| Active Ingredient: | | |
| Mexoryl SAB | 2.00 | 2.00 |
| Preservative: | | |
| Germaben II | 1.00 | 1.00 |
| Total | 100.00 | 100.00 |
| Appearance | C | C |
| pH | 2.65 | 2.90 |

L.A.S.: PEG-8 Caprylic/Capric triglicerides, GATTEFOSSÉ
Promyristyl PM-3: PPG-3 Myristyl Ether, CRODA
Procetyl-10: PPG-10 Cetyl Ether, CRODA
Mexoryl SAB: Capryloyl Salicylic Acid, L'OREAL
Germaben II: Preservative blend, SUTTON
Abbreviation: C = Clear

TABLE #2

| Phases | Wt. % | Wt. % |
| --- | --- | --- |
| Diluent: | | |
| Water | 50.00 | 47.00 |
| Coupler: | | |
| Oramix CG-110 (60%) | 42.00 | |
| Oramix NS-10 (55%) | | 45.00 |
| Solubilizer: | | |
| Procetyl-10 | 5.00 | 5.00 |
| Active Ingredient: | | |
| Mexoryl SAB | 2.00 | 2.00 |
| Preservative: | | |
| Germaben II | 1.00 | 1.00 |
| Total | 100.00 | 100.00 |

TABLE #2-continued

| Phases | Wt. % | Wt. % |
|---|---|---|
| Appearance | VCS | VCS |
| pH | 350 | 3.53 |

Oramix CG-110: Caprylyl/Capryl Glucoside, SEPPIC
Oramix NS-10: Decyl Glucoside, SEPPIC
Procetyl-10: PPG-10 Cetyl Ether, CRODA
Mexoryl SAB: Capryloyl Salicylic Acid, L'OREAL
Germaben II: Preservative blend, SUTTON
Abbreviations: VCS = Very Clear & Stable

TABLE #3

| Raw Material | Wt. % | Wt. % | Wt. % |
|---|---|---|---|
| Diluent: | | | |
| Water | 67.00 | 67.00 | 67.00 |
| Coupler: | | | |
| Cetiol HE | 25.00 | — | — |
| Glycerox 767 | — | 25.00 | — |
| Glycerox HE | — | — | 25.00 |
| Solubilizer: | | | |
| Procetyl-10 | 5.00 | 5.00 | 5.00 |
| Active Ingredient: | | | |
| Mexoryl SAB | 2.00 | 2.00 | 2.00 |
| Preservative: | | | |
| Germaben II | 1.00 | 1.00 | 1.00 |
| Total | 100 | 100 | 100 |
| Appearance | TG | C | CLG |
| pH | 2.78 | 2.97 | 2.97 |

Cetiol HE: PEG-7 Glyceryl cocoate/coco fatty acid/Gycereth-7, HENKEL CORP.
Glycerox 767: PEG-6 Capric/Caprylic triglycerides, CRODA, INC.
Glycerox HE: PEG-7 Glyceryl Cocoate, CRODA, INC.
Procetyl-10: PPG-10 Cetyl Ether, CRODA, INC.
Mexoryl SAB: Caprylolyl/Salicylic Acid, L'OREAL
Germaben II: Preservative blend, SUTTON
Abbreviations: TG: Translucent Low Viscosity Gel
C: Clear
CLG: Clear Low-Viscosity Gel

TABLE #4

| Raw Material | Wt. % | Wt. % |
|---|---|---|
| Diluent: | | |
| Water | 74.50 | 86.75 |
| Coupler: | | |
| Oramix CG-110 (60%) | 21.00 | 10.5 |
| Solubilizer: | | |
| Procetyl-10 | 2.50 | 1.25 |
| Active Ingredient: | | |
| Mexoryl SAB | 1.00 | 0.50 |
| Preservative: | | |
| Germaben II | 1.00 | 1.00 |
| Total | 100.0% | 100.0% |
| Appearance | CLEAR | CLEAR |
| pH | 3.51 | 3.51 |

Oramix CG-110 (60%): Caprylyl/Capryl Glucoside, SEPPIC
Procetyl-10: PPG-10 Cetyl Ether, CRODA, INC.
Mexoryl SAB: Capryloyl Salicylic Acid, L'OREAL
Germaben II: Preservative blend, SUTTON

TABLE #5

| Raw Material | Wt. % | Wt. % | Wt. % | Wt. % | Wt.% |
|---|---|---|---|---|---|
| Diluent: | | | | | |
| Water | 71.17 | 67.00 | 60.75 | 69.27 | 57.90 |

TABLE #5-continued

| Raw Material | Wt. % | Wt. % | Wt. % | Wt. % | Wt.% |
|---|---|---|---|---|---|
| Coupler: | | | | | |
| Oramix CG-110 (60%) | 20.83 | 25.00 | 31.25 | | |
| Oramix NS-10 (55%) | — | — | — | 22.73 | 34.10 |
| Solubilizer: | | | | | |
| Procetyl-10 | 5.00 | 5.00 | 5.00 | 5.00 | 5.00 |
| Active Ingredient: | | | | | |
| Mexoryl SAB | 2.00 | 2.00 | 2.00 | 2.00 | 2.00 |
| Preservative: | | | | | |
| Germaben II | 1.00 | 1.00 | 1.00 | 1.00 | 1.00 |
| Total | 100 | 100 | 100 | 100 | 100 |
| Appearance | PS | O | C | O | C |
| pH | — | 3.46 | 3.71 | 3.48 | 3.29 |

Oramix CG-110 (60%): Caprylyl/Capryl Glucoside, SEPPIC
Oramix NS-10 (55%): Decyl Polyglucoside, SEPPIC
Procetyl-10: PPG-10 Cetyl Ether, CRODA, INC.
Mexoryl SAB: Capryloyl Salicylic Acid, L'OREAL
Germaben II: Preservative blend, SUTTON
Abbreviations: PS = Phase Separation
O = Opaque/Translucent
C = Clear Obviously, numerous modifications of the invention as described are possible. The invention is not limited to specific embodiments described above.

What is claimed as new and is desired to be secured by Letters Patent of the United States is:

1. A composition in the form of a clear, aqueous solution, comprising water, and an effective amount of each of at least one salicylic acid compound, at least one solubilizer, and at least one coupler, whereby said clear, aqueous solution is obtained, which coupler is an alkyl polyglucoside obtained from the condensation of a $C_6$–$C_{10}$ alcohol with a glucose polymer, wherein said solubilizer is a compound of the formula:

$$R(OCH(CH_3)CH_2)_nOH$$

wherein R is a $C_8$–$C_{18}$ linear, branched or cyclic saturated aliphatic group or unsaturated aliphatic group containing one or more double bonds, and n varies from 3 to 12.

2. The composition of claim 1, wherein said at least one salicylic acid compound is a compound of the formula (I):

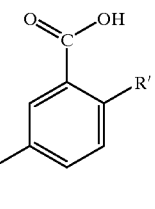

(I)

wherein:
R is a linear, branched or cyclic saturated aliphatic group or an aliphatic unsaturated group containing one or more double bonds, which are optionally conjugated, these groups containing from 2 to 22 carbon atoms and optionally substituted by at least one substituent, which is halogen, trifluoromethyl, or hydroxyl in free form or esterified by an acid having from 1 to 6 carbon atoms or a carboxyl functional group which is free or esterified by a lower alcohol having from 1 to 6 carbon atoms;

R' is hydroxyl or an ester functional group of the formula:

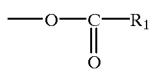

wherein $R_1$ is a linear or branched, saturated or unsaturated aliphatic group having from 1 to 18 carbon atoms.

3. The composition of claim 1, wherein said at least one salicylic acid compound is capryloyl salicylic acid.

4. The composition of claim 1, wherein said alkyl polyglucoside is obtained from the condensation of a $C_6$-alcohol with a glucose polymer.

5. The composition of claim 1, wherein said alkyl polyglucoside is obtained from the condensation of a $C_8$-alcohol with a glucose polymer.

6. The composition of claim 1, wherein said alkyl polyglucoside is obtained from the condensation of a $C_{10}$-alcohol with a glucose polymer.

7. The composition of claim 1, wherein said composition comprises 0.1–65% by weight of said at least one salicylic acid compound, 0.1–50% by weight of said solubilizer, 5–75% by weight of said coupler, and 1–94.8% by weight of water, all based on a total weight of the composition.

8. The composition of claim 1, wherein said solubilizer is present in an amount of from 1–20% by weight.

9. The composition of claim 8, wherein said solubilizer is present in an amount of 2–10% by weight.

10. The composition of claim 9, wherein said solubilizer is present in an amount of 2–8% by weight.

11. The composition of claim 1, wherein for said solubilizer, R is a $C_{10}$–$C_{18}$ linear, branched or cyclic saturated aliphatic group containing one or more double bonds, and n varies from 3 to 12.

12. The composition of claim 11, wherein R has from 10 to 16 carbon atoms.

13. The composition of claim 12, wherein R has from 12 to 16 carbon atoms.

14. The composition of claim 1, wherein n varies from 4 to 12.

15. The composition of claim 14, wherein n varies from 4 to 10.

16. A method for treating wrinkles or pigmentation of skin, or both, comprising applying an effective amount of the composition of claim 1 to the skin.

* * * * *